(12) United States Patent
Park et al.

(10) Patent No.: US 6,586,597 B1
(45) Date of Patent: Jul. 1, 2003

(54) CONTINUOUS PROCESS FOR THE PREPARATION OF OPTICALLY PURE DECAHYDROISOQUINOLINECARBOXAMIDE

(75) Inventors: Sang-Hoon Park, Taejon (KR); Byoung-Sung Kwak, Taejon (KR); Tae-Yun Kim, Taejon (KR); In-Woo Lee, Taejon (KR); Seung-Hoon Oh, Taejon (KR)

(73) Assignee: SK Corporation, Seoul (KR)

( * ) Notice: Subject to any disclaimer, the term of this patent is extended or adjusted under 35 U.S.C. 154(b) by 0 days.

(21) Appl. No.: 09/857,566
(22) PCT Filed: Dec. 15, 1998
(86) PCT No.: PCT/KR98/00428
§ 371 (c)(1), (2), (4) Date: Sep. 4, 2001
(87) PCT Pub. No.: WO00/35883
PCT Pub. Date: Jun. 22, 2000

(30) Foreign Application Priority Data

Dec. 14, 1998 (KR) ......................................... 1998-54898

(51) Int. Cl.$^7$ ............................................. C07D 217/16
(52) U.S. Cl. ...................................................... 546/146
(58) Field of Search ......................................... 546/146

(56) References Cited

U.S. PATENT DOCUMENTS 5,587,481 A   12/1996   Allen et al. .................. 546/146

FOREIGN PATENT DOCUMENTS

EP   432695   6/1991
EP   751128   1/1997

*Primary Examiner*—Patricia L. Morris
(74) *Attorney, Agent, or Firm*—Abelman, Frayne & Schwab

(57) ABSTRACT

The present invention relates to a continuous process for the preparation of [3S-(3α, 4aβ, 8aβ)]-N-tert-butyl-decahydro-3-isoquinolinecarboxamide, an intermediate useful in the synthesis of compounds for the treatment of viral diseases, from the reduction of N-tert-butyl-1,2,3,4-tetrahydro-3(S)-isoquinolinecarboxamide with a noble metal catalyst supported on inorganic oxide carrier in a fixed bed reaction system, with a high optical yield.

15 Claims, 1 Drawing Sheet

CONTINUOUS PROCESS FOR THE PREPARATION OF OPTICALLY PURE DECAHYDROISOQUINOLINECARBOXAMIDE

TECHNICAL FIELD

The present invention relates to a continuous process for the preparation of [3S-(3α,4aβ,8aβ)]-N-tert-butyl-decahydro-3-isoquinolinecarboxamide from the reduction of N-tert-butyl-1,2,3,4-tetrahydro-3(S)-isoquinolinecarboxamide with a supported noble metal catalyst in a fixed bed reaction system.

BACKGROUND ART

[3S-(3α,4aβ,8aβ)]-N-tert-butyl-decahydro-3-isoquinolinecarboxamide (hereinafter, refer to as "DHIQ") is one of the key intermediates in the synthesis of the compounds useful as antagonists of the excitatory amino acid receptor or HIV protease inhibitor for the treatment of the acquired immune deficiency syndrome (AIDS).

A process for synthesizng N-tert-butyl-1,2,3,4-tetrahydro-3(S)-isoquinolinecarbox amide (hereinafter, refer to as "TICC") by phosgenation and amination of a phenylalanine derivative is described in U.S. Pat. No. 5,587,481 to David R. Allen et al. U.S. Pat. No. 5,587,481 also teaches a method for producing DHIQ by hydrogenating HCC using 5 wt % Rh/C and/or Rh/alumina catalysts either in aqueous or organic media at 100° C. and 350 psi. After reaction, the solution should be filtered to remove the catalyst, followed by the removal of the solvent and crystallization to obtain DHIQ. However, under these reaction conditions, the yield of DHIQ is only 62 to 67% based on TICC because of the low chiroselectivity of the rhodium catalysts.

Hoffmann, EPO Application 0 432 695 A2, teaches the use of 5 wt % Rh/C catalysts in the reduction of tetrahydroisoquinoline-3-carboxylic acid to [3S-(4aS,8aS)]-decahydroisoquinoline-3-carboxylic acid in acetic acid at 80° C. and 140 atm:

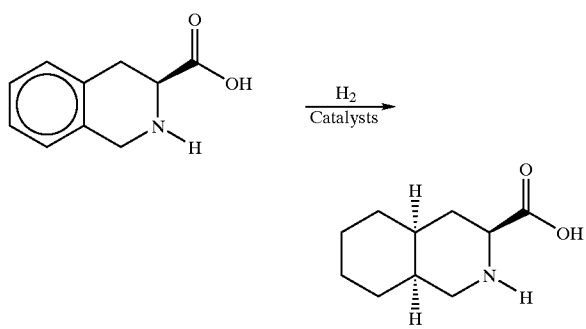

The above reaction was carried out for 24 hours. Racemization occurred and the yield of the desired enantiomer was about 65%.

Sato et al, EPO Application 0 751 128 A1, describes a process for producing DHIQ from the reduction of TICC with the use of Rh, Pt and Ru. In synthesis example 3, TICC was reduced with a 5 wt % Ru/C catalyst at 30 atm and 100° C. for 20 hours. After filtration of the catalyst and subsequent treatment, the yields of DHIQ primary crystals and secondary crystals were 52.1% and 20.7%, respectively.

Generally a batch process for the preparation of DHIQ from TICC in the prior art consists of: 1) a powder catalyst is put into a batch reactor equipped with a stirrer and heating/cooling systems; 2) the reactant in a solvent is injected to the reactor; 3) the reactor is closed and purged with an inert gas; 4) pressurized hydrogen is introduced while heating the whole content to a desired temperature; 5) hydrogen is cut and reaction is carried out until the pressure drop due to the reduction of the reactant stops; 6) after cooling to room temperature, the product in the solvent is discharged.

As is manifest for those who are skilled in the art, the disadvantages of the above batch processes are: 1) the process inherently is not productive and is complicated owing to the adoption of batch reactors; 2) it is difficult to precisely control the reaction conditions, for example, hydrogen partial pressure, because the process is dynamic; 3) it requires a series of post-treatment processes to recover and to reuse powder catalysts; 4) it is in danger of the fire and explosion because the catalyst having already reduced is used; and 5) the yield of DHIQ is not good.

DISCLOSURE OF INVENTION

The intensive and thorough research of the present inventors for solving the above problems encountered in prior arts results in the development of a new process superior in optical yield.

Therefore, it is an object of the present invention to provide a process for the preparation of optically active [3S-(3α,4aβ,8aβ)]-N-tert-butyl-decahydro-3-isoquinoline carboxamide, an intermediate useful in the synthesis of compounds for the treatment of viral diseases, by the continuous reduction of N-tert-butyl-1,2,3,4-tetrahydro-3(S)-isoquinolinecarboxamide with a supported noble metal catalyst in a fixed bed reaction system with a high optical yield.

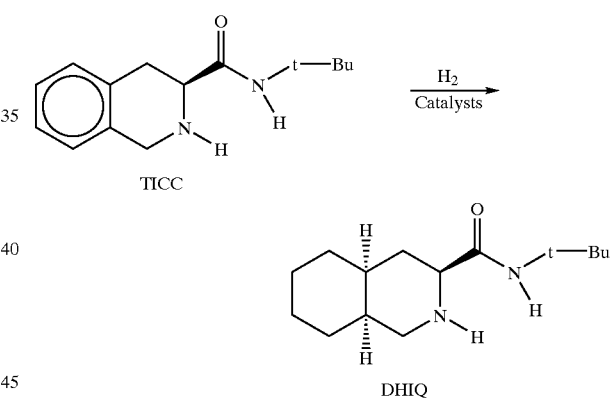

In accordance with an aspect of the present invention, there is provided a method for preparing [3S-(3α,4aβ,8aβ)]-N-tert-butyl-decahydro-3-isoquinolinecarboxamide from N-tert-butyl-1,2,3,4-tetrahydro-3(S)-isoquinolinecarboxamide with a high optical yield, comprising continuously reducing N-tert-butyl-1,2,3,4-tetrahydro-3(S)-isoquinoline carboxamide dissolved in an organic solvent to [3S-(3α,4aβ,8aβ)]-N-tert-butyl-decahydro-3-isoquinolinecarboxamide with hydrogen in a fixed bed reactor charging a noble metal catalyst supported on an inorganic oxide carrier with the range of the metal content between 0.5 and 10 wt %, at a temperature in the range of about 50 and 200° C., under the pressure in the range of about 300 and 2,500 psig and at the WHSV in the range of about 0.1 and 10 $h^{-1}$, wherein the molecular ratio of hydrogen to N-tert-butyl-1,2,3,4-tetrahydro-3(S)-isoquinolinecarboxamide is in the range of about 4 and 10, N-tert-butyl-1,2,3,4-tetrahydro-3(S)isoquinolinecarboxamide content in the organic solvent is in the range of about 2 and 50 wt % and the inorganic oxide carrier has the BET surface area in the range of about 10 and 1,000 $m^2/g$, the median pore diameter of the major pores of less than 200 Å and the total pore volume in the range of about 0.2 and 1.2 cc/g.

The starting material in the present invention is a carboxamide of isoquinoline, N-tert-butyl-1,2,3,4-tetrahydro-3 (S)-isoquinolinecarboxamide (TICC), which can be prepared by either a multi-step synthesis process including phosgenation and amination of a phenylalanine derivative (Allen, D.R., et al, U.S. Pat. No. 5,587,481) or by any other similar methods (Sato, T., et al., EPO Application 0 751 128 A1). To obtain DHIQ with a high optical yield, TICC with following specifications is preferred: (1) chromatographic purity by gas chromatography: not less than 99.2%; (2) R(+) enantiomer by chiral HPLC: not more than 1.0%; (3) melting point (range): 92~100° C.

To achieve a higher space time yield, to reuse the catalyst repeatedly without post-treatment steps and to reduce the workup steps, the reaction is performed in a fixed bed reactor in the present invention. There is no limitation in the type of the fixed bed reactor and the direction of the reactant flow. However, the reaction is preferably carried out in a trickle-bed type reactor with a down-flow mode of both hydrocarbon(s) and hydrogen to facilitate the contact between the reactants. The reactor should be equipped with suitable devices to evenly distribute all the reactants.

The reaction should be carried out in a solvent medium to easily pump TICC into the reactor and to remove the reaction heat easily as the reduction is highly exothermic. Hydrocarbons that do no react with hydrogen and TICC and can dissolve TICC substantially may be used as solvents. As a solvent of the present invention, any type of a single hydrocarbon or a mixture thereof, e.g., acetic acid, propionic acid, butyric acid, or isobutyric acid, methyl alcohol, ethyl alcohol, n-propyl alcohol, i-propyl alcohol, n-butyl alcohol, sec-butyl alcohol, tert-butyl alcohol, methyl acetate, ethyl acetate, n-propyl acetate, i-propyl acetate, n-butyl acetate, n-hexane, i-hexane, n-heptane, i-heptane, n-octane, or i-octane, can be used. But preferably, n-propyl alcohol, i-propyl alcohol, sec-butyl alcohol, tert-butyl alcohol, ethyl acetate, n-butyl acetate, n-hexane, or n-heptane is used. More preferably, i-propyl alcohol, tert-butyl alcohol, ethyl acetate, n-butyl acetate, n-hexane, or n-heptane is used. Most preferably, ethyl acetate, n-butyl acetate, n-hexane, or n-heptane is used. The concentration of TICC is 2 to 50 wt % in an organic solution. Preferably the concentration is 5 to 30 wt %. Depending on the concentration of TICC, the solvent may be heated to dissolve all solid particles. During dissolving TICC, TICC solution should not be injected to the reactor. So two TICC dissolving reactors or more should be prepared and alternatively operated in order to provide the reactor with fully dissolved TICC.

TICC can be reduced to DHIQ using molecular hydrogen and a supported noble metal catalyst. As a support, any inorganic oxide, e.g., alumina, silica, silica-alumina, zirconia, titania, or molecular sieves, is suitable. Among these inorganic materials, alumina and silica are preferred. The support may have a BET surface area between 10 and 1,000 m$^2$/g. Preferably, the BET area of the support is 20 to 500 m$^2$/g and most preferably is 50 to 300 m$^2$/g. The pore volume of the support is preferably 0.2 to 1.2 cc/g, more preferably 0.3 to 1.0 cc/g. There is no limitation in the pore size distribution of the support, but the support with median pore diameter of the major pores of less than 200 angstroms (Å), measured by nitrogen adsorption/desorption, is preferable. More preferably the median pore diameter of the support is less than 150 Å. The shape of the support particle may be circular, cylindrical, granular, or in any other form. But to have suitable mechanical properties, a pellet of either circular or cylindrical type is preferred.

As a noble metal, Pd, Pt. Ru, Rh, Os, or a mixture thereof is suitable. Preferably Ru, or Os is used. The concentration of the noble metal(s) is preferably between 0.5 and 10 wt %, more preferably between 1 and 6 wt %. When the metal content is lower than 0.5 wt %, the activity and the selectivity to DHIQ are low. When the metal content is higher than 10 wt %, the price of metal makes the process uneconomic. The metal is supported onto the support by any suitable method, e.g., incipient wetness impregnation, excess water impregnation, spraying, or mechanical mixing. After the metal is loaded, the catalyst is calcined in air or in an inert gas atmosphere at a temperature between 300 and 700° C. for more than two hours. Preferably the calcination temperature is 350 to 600° C. When the temperature is below 300° C., calcination is incomplete and the precursor compound may not be decomposed. When the temperature is higher than 700° C., the metal dispersion is too low to have a substantial catalytic activity. After the catalyst is loaded, the catalyst should be reduced with flowing hydrogen at a temperature between 50 and 400° C. for at least one hour depending on the metal employed in the catalyst.

The reduction of TICC to DHIQ is carried out at 300 to 2,500 psig, 50 to 200° C., and the weight hourly space velocity (WHSV) of 0.1 to 10 h$^{-1}$. Preferably DHIQ is prepared at 500 to 2,000 psig, 80 to 170° C., and the WHSV of 0.2 to 6 h$^{-1}$. More preferably, the reaction is performed at 800 to 1,600 psig, 100 to 160° C., and the WHSV of 0.5 to 4 h$^{-1}$. When the reaction is carried out at a condition out of above ranges, the yield is low and the catalyst deactivates rather rapidly, thus the advantage of continuous reduction disappears.

There is no limitation in the molecular ratio of hydrogen to TICC if only it exceeds three to ensure 100% conversion of TICC. However, when considering the economics, the ratio is preferably between 4 and 10. Hydrogen in excess of the reaction stoichiometry may be discharged or recompressed by recycle compressor and recycled to the reactor.

Reaction products coming out of the reactor is fed to a solvent recovering apparatus where at least apart of solvent is separated from the rest of the product. The apparatus can be of any type, e.g., a distillation tower or flash vaporizer. The bottom DHIQ product, or a concentrate, is sent to a crystallizer. A hydrocarbon solvent, e.g., hexane or heptane is used during the crystallization.

BEST MODE FOR CARRYING OUT THE INVENTION

Figure 1:
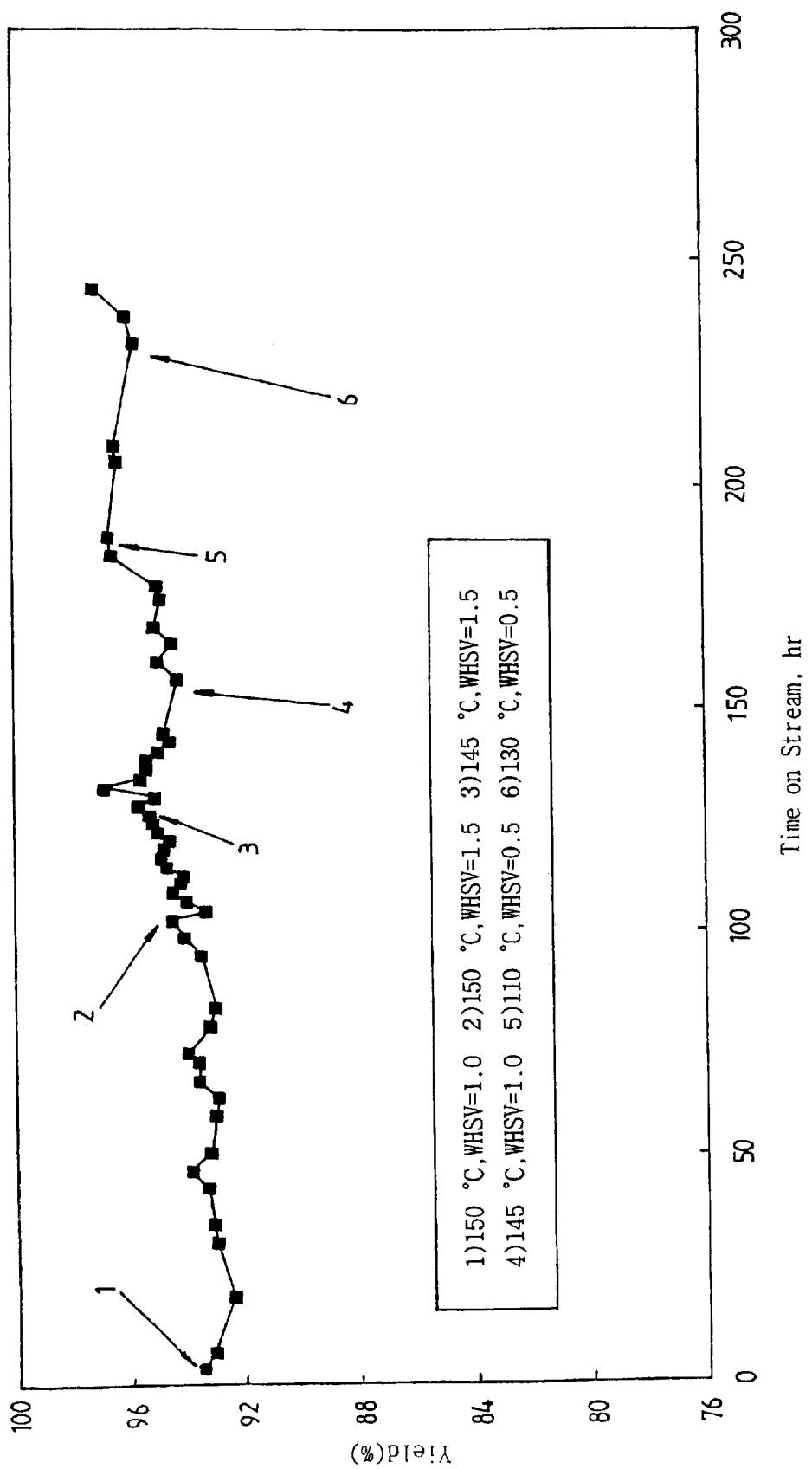
FIG. 1 is a graph illustrating the relationship between yield and time on stream using a process and catalyst in accordance with the present invention.

The following examples describe the present invention in detail for purposes of illustration and should not be construed as being limited by procedures hereafter specified.

PREPARATION EXAMPLE I

Preparation of Catalysts 6.35 g of ruthenium chloride (Aldrich, RuCl$_3$) was dissolved with 40 cc of doubly-distilled water in a 100 cc volumetric flask. Onto 100 g of Norton SA 3177 alumina (surface area: 100 m$^2$/g; pore volume: 0.49 cc/g; median pore diameter 100 Å), which was in a small tumbler connected to a variable speed motor, the solution containing Ru was evenly sprayed while rotating the tumbler at the speed of 50 rpm. After loading the metal, the catalyst was calcined in a muffle furnace at 550° C. for 6 hours. The analysis with X-ray fluorescence showed the Ru content of 3.0 wt %.

PREPARATION EXAMPLES II~IV

Preparation of Catalysts

All the procedures are similar to those in Preparation Example I except for the use of 100 g of different support materials (TABLE 1).

TABLE I

| Prep. Example No. | Support | Surface area m²/g | Pore volume cc/g | Med. pore diam. Å |
|---|---|---|---|---|
| Prep. Example II | Norton 6173 | 220 | 0.62 | 70 |
| Prep. Example III | Norton 6176 | 255 | 1.14 | 70/5,000 |
| Prep. Example IV | Norton silica | 144 | 0.78 | 80/400 |

PREPARATION EXAMPLES V~VI

Preparation of Catalysts

All the procedures are similar to those in Preparation Example I except for the use of corresponding amounts of ruthenium nitrosyl nitrate (Aldrich, 1.5% Ru). As a support, Norton 3177 (Preparation Example V) or 6173 (Preparation Example VI) was used, respectively. In these cases, the spraying-drying steps were repeated a few times to have the desired metal content of 3 wt %.

EXAMPLE I

Into a 316 stainless steel reactor (2.54 cm ID×60 cm L) on a full automatic high pressure reaction system was charged 50 g of catalyst (⅛ cylindrical pellet) prepared in Preparation Example I. After a leak test and purging with nitrogen, hydrogen flow of 1 slpm was applied to the reactor while increasing the temperature from room temperature to 300° C. at the rate of 1° C./min. After holding the temperature at 30° C. for 2 hours, the reactor was cooled to 150° C. Then 10 wt % TICC in a solvent was pumped to the reactor at a WHSV and pressure specified in TABLE II with a two-fold excess amount of hydrogen. Samples were taken every 4 hours on steam and analyzed with a FID GC (60 m×0.25 mm×0.25 μm β-DEX 120 column). All the data specified in TABLE II were taken at 100 hours on stream.

TABLE II

| Catalyst | T °C. | P psig | WHSV H⁻¹ | Solvent | Conversion % | Sel. To DHIQ % |
|---|---|---|---|---|---|---|
| Prep. Example I | 110 | 1350 | 0.5 | butyl acetate | 100 | 96.5 |
| Prep. Example I | 120 | 1500 | 2.0 | butyl acetate | 99.0 | 91.0 |
| Prep. Example I | 133 | 1500 | 3.0 | butyl acetate | 100 | 92.5 |
| Prep. Example I | 145 | 1350 | 1.5 | butyl acetate | 100 | 95.4 |
| Prep. Example I | 150 | 996 | 0.5 | butyl acetate | 90.1 | 91.0 |
| Prep. Example I | 150 | 996 | 0.5 | heptane | 90.0 | 89.7 |
| Prep. Example I | 150 | 1350 | 0.5 | butyl acetate | 96.7 | 91.5 |
| Prep. Example I | 150 | 1350 | 1.0 | butyl acetate | 100 | 93.3 |
| Prep. Example I | 150 | 1350 | 1.5 | butyl acetate | 100 | 94.4 |
| Prep. Example I | 160 | 1500 | 3.0 | butyl acetate | 100 | 90.0 |
| Prep. Example II | 150 | 996 | 0.5 | butyl acetate | 95.3 | 86.4 |
| Prep. Example III | 150 | 996 | 0.5 | butyl acetate | 98.0 | 86.1 |
| Prep. Example IV | 140 | 1350 | 1.5 | butyl acetate | 100 | 92.6 |
| Prep. Example IV | 150 | 996 | 0.5 | butyl acetate | 96.3 | 90.0 |
| Prep. Example IV | 150 | 996 | 0.5 | ethyl acetate | 95.7 | 90.5 |
| Prep. Example IV | 150 | 1350 | 0.5 | butyl acetate | 97.6 | 87.1 |
| Prep. Example IV | 150 | 1350 | 1.5 | butyl acetate | 100 | 89.3 |
| Prep. Example V | 150 | 996 | 0.5 | butyl acetate | 80.0 | 87.5 |
| Prep. Example VI | 150 | 996 | 0.5 | butyl acetate | 94.7 | 86.4 |
| Prep. Example VI | 150 | 996 | 0.5 | i-propanol | 95.6 | 84.5 |

COMPARATIVE EXAMPLES I~IV

Uncontrolled

Reaction tests were carried out in butyl acetate at 150° C., 996 psig, and the WHSV of 0.5 h⁻¹ in the same manner as in the Example I except for the catalyst employed (TABLE III). The catalyst was the conventional commercial catalyst.

TABLE III

| Comp. Example No. | Catalyst | Conversion % | Sel. To DHIQ % |
|---|---|---|---|
| Comp. Exam. I | Johnson Matthey 2% Ru/C | 93.0 | 67.5 |
| Comp. Exam. II | Degussa H257 2% Ru/alumina, Lot: CC4-243 | 94.9 | 83.0 |
| Comp. Exam. III | Chemcat 2% Ru/alumina, Lot: 456-67020 | 77.5 | 82.5 |
| Comp. Exam. IV | Johnson Matthey 3% Ru/silica | 82.8 | 74.2 |

EXAMPLE II

The reaction was carried out in a similar reaction system to that in Example I using 150 g of the catalyst prepared by following the method described in Preparation Example I. 150 g of 3% Ru on Norton 3177 alumina were charged in a fixed bed reactor. After purging with nitrogen and reduction of the catalyst at 300° C., a 10 wt % TICC in butyl acetate solution was pumped to the reactor at 150° C., 1,350 psig, and the WHSV of 1.0 h⁻¹. During the reaction, the pressure was kept at 1350 psig while varying the temperature and WHSV as shown in FIG. 1. FIG. 1 is a graph illustrating the relationship between yield and time on stream using a process and catalyst in accordance with Example II. As shown in FIG. 1, no deactivation was observed for more than 10 days.

41 liters of butyl acetate solution containing DHIQ (purity 92.2 wt %) were collected after reaction for 200 hours and were put into a 50 liter glass reactor equipped with a refrigeration system to get crystals of DHIQ. After evaporating about 90% of butyl acetate in the solution, 15 liters of n-heptane were added into the reactor. Then the reactor was slowly cooled from 60° C. to −10° C. at a rate of 0.5° C./min. The yield of the primary crystals was 73%. The procedure was repeated to get the secondary crystals with the yield of 19%. The optical purity of the crystals was 99.5%.

Optical rotation: $[\alpha]^D 20 = -72.60°$; melting point: 114.3° C. (spread 112–115° C.)

The yield of the present continuous hydrogenation process is higher than that of the prior art batch process such as U.S. Pat. No. 5,587,481 (yield: 62–67%) and EPO Application 0 751 128 (primary crystals: 52.1 wt %, secondary crystals: 20.7 wt %).

A number of alternative embodiments and variations will be apparent to those skilled in the art. Therefore, the aforementioned description should not be interpreted to limit the invention.

We claim:

1. A method of preparing [3S-(3α,4aβ,8aβ)]-N-tert-butyl-decahydro-3-isoquinoline carboxamide from N-tert-butyl-1,2,3,4-tetrahydro-3(S)-isoquinolinecarboxamide with a high optical yield, comprising continuously reducing N-tert-butyl-1,2,3,4tetrahydro-3(S)-isoquinolinecarboxamide dissolved in an inorganic solvent to [3S-(3α,4aβ,8aβ)]-N-tert-butyl-decahydro-3-isoquinolinecarboxamide with hydrogen in a fixed bed reactor charging a noble metal catalyst supported on an inorganic oxide carrier with the range of the metal content between 0.5 and 10 wt %, at a temperature in the range of about 50 and 200° C., under the pressure in the range of about 300 and 2,500 psig and at the WHSV in the range of about 0.1 and 10 $h^{-1}$, wherein the molecular ratio of hydrogen to N-tert-butyl-1,2,3,4tetrahydro-3(S)-isoquinolinecarboxamide is in the range of about 4 and 10, N-tert-butyl-1,2,3,4-tetrahydro-3(S)-isoquinolinecarboxamide content in an organic solvent is in the range of about 2 and 50 wt % and the inorganic oxide carrier has the BET surface area in the range of about 10 and 1,000 $m^2$/g, the median pore diameter of the major pores of less than 200 Å and the total pore volume in the range of about 0.2 and 1.2 cc/g.

2. The method of claim 1 wherein the temperature is in the range of about 80° C. and 170° C., the pressure is in the range of about 500 and 2,000 psig and the WHSV is in the range of about 0.2 and 6 $h^{-1}$.

3. The method of claim 2 wherein the temperature is in the range of about 100° C. and 160° C., the pressure is in the range of about 800 and 1,600 psig and the WHSV is in the range of about 0.5 and 4 $h^{-1}$.

4. The method of claim 1 wherein the N-tert-butyl-1,2,3,4-tetrahydro-3(S)-isoquinoline carboxamide content in the organic solvent is in the range of about 5 and 30 wt %.

5. The method of claim 1 wherein the organic solvent is at least one selected from the group consisting of acetic acid, propionic acid, butyric acid, isobutyric acid, methyl alcohol, ethyl alcohol, n-propyl alcohol, i-propyl alcohol, n-butyl alcohol, sec-butyl alcohol, tert-butyl alcohol, methyl acetate, ethyl acetate, n-propyl acetate, i-propyl acetate, n-butyl acetate, n-hexane, i-hexane, n-heptane, i-heptane, n-octane, and i-octane.

6. The method of claim 5 wherein the organic solvent is at least one selected from the group of i-propyl alcohol, tert-butyl alcohol, ethyl acetate, n-butyl acetate, n-hexane, and n-heptane.

7. The method of claim 6 wherein the organic solvent is at least one selected from the group of ethyl acetate, n-butyl acetate, n-hexane, and n-heptane.

8. The method of claim 1 wherein the noble metal is ruthenium or osmium.

9. The method of claim 1 wherein the metal content is in the range of about 1 and 6 wt %.

10. The method of claim 1 wherein the inorganic oxide carrier is selected from the group consisting of alumina, silica, silica-alumina, zirconia, titania, and molecular sieves.

11. The method of claim 10 wherein the inorganic oxide carrier is alumina or silica.

12. The method of claim 1 wherein the BET surface area of the inorganic oxide carrier is in the range of about 20 and 500 $m^2$/g.

13. The method of claim 12 wherein the BET surface area of the inorganic oxide carrier is in the range of about 50 and 300 $m^2$/g.

14. The method of claim 1 wherein the total pore volume of the inorganic oxide carrier is in the range of about 0.3 and 1.0 cc/g.

15. The method of claim 1 wherein the fixed bed reactor is a trickle-bed reactor type.

* * * * *